United States Patent [19]

Bolich, Jr.

[11] 4,452,732

[45] Jun. 5, 1984

[54] SHAMPOO COMPOSITIONS

[75] Inventor: Raymond E. Bolich, Jr., Maineville, Ohio

[73] Assignee: The Procter & Gamble Company, Cincinnati, Ohio

[21] Appl. No.: 446,840

[22] Filed: Dec. 6, 1982

Related U.S. Application Data

[63] Continuation of Ser. No. 274,009, Jun. 15, 1981, abandoned.

[51] Int. Cl.$^3$ ................................................ C11D 1/62
[52] U.S. Cl. ...................................... 252/547; 252/545; 252/117; 252/DIG. 13; 252/DIG. 14; 424/70
[58] Field of Search ............... 252/547, 545, 546, 548, 252/DIG. 13, 117, DIG. 14; 424/70

[56] References Cited

U.S. PATENT DOCUMENTS

| | | | |
|---|---|---|---|
| 3,156,656 | 11/1964 | Libby | 252/DIG. 13 |
| 3,223,645 | 12/1965 | Kalberg | 252/117 |
| 3,274,106 | 9/1966 | Smiens | 252/547 |
| 3,711,414 | 1/1973 | Hewitt | 252/DIG. 13 |
| 4,102,825 | 6/1978 | Murate et al. | 252/DIG. 13 |
| 4,379,753 | 4/1983 | Bolich, Jr. | 252/DIG. 13 |

OTHER PUBLICATIONS

Solubility-Temperature Coefficient, Surface Active Agents, Schwartz & Perry, pp. 302-303, 1949, Interscience Publisher, Inc., New York.

*Primary Examiner*—John E. Kittle
*Assistant Examiner*—Hoa Van Le
*Attorney, Agent, or Firm*—Richard C. Witte; John V. Gorman; Douglas C. Mohl

[57] ABSTRACT

Shampoo compositions containing unsaturated quaternary ammonium compounds which compositions exhibit improved low temperature stability due to the inclusion of a long chain acyl derivative.

8 Claims, No Drawings

SHAMPOO COMPOSITIONS

CROSS REFERENCE TO RELATED APPLICATION

This is a continuation of of my copending application Ser. No. 274,009, filed June 15, 1981, now abandoned.

TECHNICAL FIELD

The present invention is related to stable conditioning shampoos containing an unsaturated long chain quaternary ammonium compound and a long chain acyl derivative.

BACKGROUND ART

The use of unsaturated quaternary compounds in a variety of compositions is well known. U.S. Pat. No. 3,117,113, Jan. 6, 1964 to Tudor discloses the use of unsaturated quaternary compounds in vinyl chloride compositions. U.S. Pat. No. 3,282,849, Nov. 1, 1966 to Diehm et al discloses germicidal cleansing compositions which contain unsaturated quaternary compounds. U.S. Pat. No. 3,577,528, May 4, 1971 to McDonough et al discloses unsaturated quaternary compounds in a two-phase conditioner product. U.S. Pat. No. 3,849,348, Nov. 19, 1974 to Hewitt discloses detergent compositions containing a betaine and amine oxide surfactant system along with an unsaturated quaternary.

It is also disclosed in the prior art that long chain acyl derivatives are useful in compositions such as shampoos. U.S. Pat. No. 3,990,991, Nov. 9, 1976 to Gerstein discloses shampoos containing a cationic material and ethylene glycol distearate. U.S. Pat. No. 4,061,602, Dec. 6, 1977 to Oberstar et al discloses conditioning shampoos containing a cationic polymer and a polyethylene glycol distearate. U.S. Pat. No. 4,110,263, Aug. 29, 1978 to Lindemann discloses detergent compositions containing alkylene oxylated bisquaternary compounds and a polyethylene glycol distearate. U.S. Pat. No. 4,138,371, Feb. 6, 1979 to Verdiccio discloses shampoo compositions containing a quaternized polymer and a polyethylene glycol distearate.

While the above described references disclose compositions containing components of the type used in the present compositions, they do not teach or suggest the stability problems associated with unsaturated quaternary compounds found by Applicant.

In addition the references fail to teach or suggest combining unsaturated quaternary compounds with long chain acyl derivatives in a single composition.

It is, therefore, an object of the present invention to provide stable hair conditioning shampoo compositions.

It is a further object of the present invention to provide shampoo compositions containing an unsaturated quaternary ammonium compound and a long chain acyl derivative.

These other objects will become more apparent from the detailed description which follows.

Unless otherwise indicated, all percentages herein are by weight.

DISCLOSURE OF THE INVENTION

The compositions of the present invention comprise a quaternary ammonium compound having at least one unsaturated long chain substituent, from about 1% to about 6% of a long chain acyl derivative, from about 10% to about 30% of a surfactant and from about 50% to about 80% water.

DETAILED DESCRIPTION OF THE INVENTION

The essential as well as optional components of the present compositions are described in detail below.

Quaternary Ammonium Compound

The unsaturated quaternary ammonium compounds useful in the present compositions have at least one and preferably two long chain hydrocarbon groups. By "unsaturated" herein is meant having an iodine value of from about 10 to about 85, preferably 20 to about 50.

The chains contain an average of from about 16 to about 22, preferably from about 16 to about 18, carbon atoms. The remaining groups, if any, attached to the quaternary nitrogen atom, are preferably $C_1$ to $C_4$ alkyl or hydroxyalkyl groups. Although it is true that at least one of the long chains is unsaturated, as above described, these chains may also contain heteroatoms or other linkages, such as hydroxy groups and ester, amide or ether linkages, as long as each chain falls within the required carbon atom ranges. Preferred quaternary ammonium compounds are those having the formulae

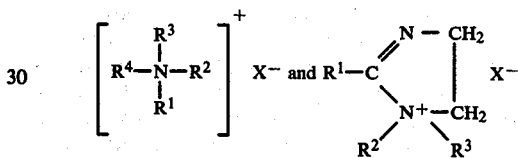

wherein the $R^1$ and $R^2$ groups contain an average of from about 16 to 22 carbon atoms, most preferably from about 16 to about 18 carbon atoms, $R^3$ and $R^4$ are $C_1$ to $C_4$ alkyl or hydroxyalkyl groups, and X is any compatible anion, particularly one selected from the group consisting of halide, hydroxide, methylsulfate, or acetate anions. Mixtures of these agents are also useful in the present invention.

Preferred quaternary compounds include di-partially hydrogenated tallow dimethyl-ammonium halide (especially chloride) which is also known as di-softened tallow alkyl dimethylammonium halide. A commercially available compound of this type is Adogen 470DE, sold by Sherex Chemical Company which has an iodine value of about 29.

Other preferred quaternary compounds include dioleyl dimethylammonium chloride and methyl-1-oleyl amido ethyl-2-oleyl imidazolinium methylsulfate.

The level of quaternary compound useful in the present compositions is based on the amount of betaine and sultaine surfactant used in the compositions. The amount of quaternary is generally from about 15% to about 50%, preferably from about 20% to about 40%, of those surfactants.

Acyl Derivative

The long chain ($C_{16}$ or longer) acyl derivatives useful in the compositions are long chain amides, alkanolamides, esters of ethylene glycol and glycerine, esters of carboxylic acids (melt point >50° C.), esters of thiodicarboxylic acids, and mixtures of these derivatives. Examples of such derivatives include ethylene glycol distearate, stearyl stearate, stearic monoethanolamide (stearamide MEA), and distearyl dithiopropionate. It is readily apparent that many other materials meet the general descriptions above.

The acyl derivative is used at a level of from about 1% to about 6%, preferably from about 1% to about 4%, in the compositions of the present invention.

Surfactant

The essential surfactants used in the compositions of the present invention are higher alkyl betaines and mixtures of betaines and sultaines.

The betaines may be represented by the following structural formula

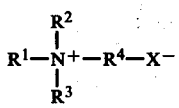

wherein $R^1$ is a long chain alkyl radical having from about 10 to about 18 carbon atoms or the amido radical

Wherein $R^5$ is a long chain alkyl radical, $R^2$ and $R^3$ are each alkyl radicals having from about 1 to about 3 carbon atoms, $R^4$ is an alkylene or hydroxy alkylene radical having from about 1 to about 4 carbon atoms, and X is a carboxylate radical. $R^1$ and $R^5$ may be a mixture of long chain alkyl radicals and may contain one or more intermediate linkages or non-functional substituents such as hydroxyl or halogen radicals which do not affect the hydrophobic character of the radical. Examples of betaines useful herein include cocodimethyl carboxymethyl betaine (cocobetaine), lauryldimethyl carboxymethyl betaine (lauryl betaine), cetyl dimethyl carboxymethyl betaine (cetyl betaine), coco amidopropyl dimethyl carboxymethyl betaine (cocoamido propyl betaine), etc.

The sultaines are betaines of the type described above except that a sulfonate radical is present in place of the carboxylate radical. Examples of sultaines useful herein are cocodimethyl sulfopropyl betaine (coco sulfopropyl betaine), coco amidopropyl sulfopropyl betaine (coco amidosulfopropyl betaine), lauryl dimethyl sulfopropyl betaine (lauryl sulfopropyl betaine), etc. The amount of surfactant is from about 10% to about 30%, preferably from about 15% to about 25%.

Water

Water is the final essential ingredient of the present invention and is present at a level of from about 50% to about 80%, preferably from about 60% to about 75%.

Optional Components

The shampoos herein can contain a variety of nonessential optional ingredients suitable for rendering such compositions more stable and desirable. Such conventional optional ingredients are well known to those skilled in the art, e.g., preservatives such as benzyl alcohol, methyl paraben, propyl paraben and imidazolidinyl urea; other quaternary ammonium compounds which do not meet the above-described unsaturation requirement such as distearyl dimethyl ammonium chloride; thickeners and viscosity and modifiers such as coconut ethanol amide, sodium chloride, sodium sulfate, methylcellulose, polyvinyl alcohol, and ethyl alcohol; pH adjusting agents such as citric acid, succinic acid, phosphoric acid, sodium hydroxide, sodium carbonate, etc.; suspending agents such as hydrogenated castor oil; perfumes; dyes; and, sequestering agents such as disodium ethylenediamine tetraacetate. Such agents generally are used individually at a level of from about 0.01% to about 3% by weight of the compositions. The pH of the instant compositions is from about 5 to about 8.

METHOD OF MANUFACTURE

The shampoos of the present invention may be made in a variety of ways. A preferred method is set forth in Example I.

INDUSTRIAL APPLICABILITY

The present compositions are used in a conventional manner for cleaning hair.

The following Examples further describe and demonstrate the preferred embodiments within the scope of the present invention. The Examples are given solely for the purpose of illustration and are not to be construed as limitations of the present invention as many variations thereof are possible without departing from its spirit and scope. Unless otherwise indicated, all percentages herein are by weight.

EXAMPLE I

The following composition of the present invention was prepared:

| Ingredient | Wgt. % |
|---|---|
| Aerosol 30[1] | 35.70 |
| Standapol AB-45[2] | 21.75 |
| Adogen 470DE[3] | 5.25 |
| Stearyl dimethyl benzyl ammonium chloride (stearalkonium chloride) | 1.00 |
| Cocamide DEA | 2.00 |
| Perfume | 0.75 |
| Formalin | 0.03 |
| Conc. HCl | 0.20 |
| Ethylene glycol distearate | 1.00 |
| Dist. Water | q.s. |

[1]Cocoamidopropyl betaine (30% active) - American Cyanamid Co.
[2]Coco-betaine (35% active), Henkel Corp.
[3]Di-softened tallow dimethyl ammonium chloride (75% active) - Sherex Chemical Co.

Preparation For Example I

To a one liter mix tank was added 357 grams of Aerosol 30, 217.5 grams of Standapol AB-45, 52.5 grams of Adogen 470DE, 10 grams of stearalkonium chloride, 20 grams of cocamide DEA, 7.5 grams of perfume, 0.3 grams of Formalin, 2 grams of conc. HCl (37%), 10 grams of ethylene glycol distearate, and 323.2 grams of distilled water. The contents of the mix tank were heated with agitation (magnetic stirring hot plate) to about 160° F., held there for about 15 minutes, and then allowed to cool to room temperature with gentle agitation. The resulting product shows no instability at 50° F. The same product without EGDS shows physical separation at 50° F. within 1-3 months.

EXAMPLE II

The following composition of the present invention was prepared in the manner described in Example I.

| Ingredient | Wgt. % |
|---|---|
| Aerosol 30 | 29.95 |
| Standapol AB-45 | 24.50 |
| Adogen 470DE | 10.75 |

-continued

| Ingredient | Wgt. % |
| --- | --- |
| Perfume | 0.75 |
| Formalin | 0.03 |
| Conc. HCl | 0.10 |
| Ethylene glycol distearate | 2.00 |
| Dist. Water | q.s. |

EXAMPLE III

The following composition of the present invention is prepared in the manner described in Example I.

| Ingredient | Wgt. % |
| --- | --- |
| Tegobetaine L-7[1] | 55.00 |
| Varisoft 3690[2] | 6.00 |
| Cocamide MEA | 1.00 |
| Perfume | .50 |
| Formalin | .03 |
| Distearyl thiodipropionate | 2.50 |
| Dist. Water | q.s. |

[1] Cocoamidopropyl betaine (30%), Goldschmidt Products Corp.
[2] Methyl-1-oleyl amido ethyl-2-oleyl imidazolinium-methyl sulfate - 75% active, Sherex Chemical Company.

EXAMPLE IV

The following composition of the present invention is prepared in the manner described in Example I.

| Ingredient | Wgt. % |
| --- | --- |
| Standapol AB-45 | 20.00 |
| Lonzaine CS[1] | 20.00 |
| Adogen 472[2] | 9.00 |
| Lauramide DEA | 1.50 |
| Formalin | .03 |
| Perfume | .25 |
| Ethylene glycol monostearate | 5.00 |
| Conc. HCl | 0.25 |
| Dist. Water | q.s. |

[1] Cocoamidopropyl sultaine (50%) Lonza, Inc.
[2] Dioleyl dimethyl ammonium chloride, 75% active, Sherex Chemical Company.

EXAMPLE V

The following composition of the present invention is prepared in the manner described in Example I.

| Ingredient | Wgt. % |
| --- | --- |
| Aerosol 30 | 35.70 |
| Standapol AB-45 | 21.75 |
| Andogen 470DE | 4.00 |
| Cocamide DEA | 3.00 |
| Perfume | 0.75 |
| Formalin | 0.03 |
| Conc. HCl | .10 |
| Stearamide MEA stearate | 2.00 |
| Dist. Water | q.s. |

What is claimed is:
1. A shampoo composition comprising:
    (A) a quaternary ammonium compound having at least one unsaturated long chain substituent and having an iodine value of from about 10 to about 85;
    (B) from about 1% to about 6% of a long chain acyl derivative selected from the group consisting of long chain amides, alkanol amides, esters of glycerine, esters of ethylene glycol, esters of carboxylic acids, esters of thiocarboxylic acids and mixtures thereof;
    (C) from about 10% to about 25% of a surfactant selected from the group consisting of higher alkyl betaines and mixtures of higher alkyl betaines and higher alkyl sultaines; and,
    (D) from about 50% to about 80% water;
wherein said quaternary compound is present at a level equal to from about 15% to about 40% of the level of said surfactant.
2. A shampoo composition according to claim 1 wherein the long chain acyl derivative is present at a level of from about 1% to about 4%.
3. A shampoo composition according to claim 2 wherein the quaternary ammonium compound is present at a level equal to from about 20% to about 40% of the level of the betaine or the betaine and sultaine mixture.
4. A shampoo composition according to claim 3 wherein the surfactant is present at a level of from about 15% to about 25%.
5. A shampoo composition according to claim 4 wherein the acyl derivative is selected from the group consisting of ethylene glycol distearate, ethylene glycol monostearate, stearyl stearate, stearic monoethanolamide, and distearyl dithiopropionate.
6. A shampoo composition according to claim 5 wherein the quaternary ammonium compound is selected from the group consisting of di-softened tallow dimethylammonium chloride, dioleyl dimethylammonium chloride, methyl-1-oleyl amido ethyl-2-oleyl imidazolinium methyl sulfate and mixtures thereof.
7. A shampoo composition according to claim 6 wherein the surfactant is selected from the group consisting of cocoamidopropyl betaine, coco betaine, cocoamidopropyl sultaine and mixtures thereof.
8. A shampoo composition according to claim 7 wherein the acyl derivative is ethylene glycol distearate and the quaternary ammonium compound is di-softened tallow dimethyl ammonium chloride.

* * * * *